(12) United States Patent
Xia et al.

(10) Patent No.: US 9,557,212 B2
(45) Date of Patent: Jan. 31, 2017

(54) DETERMINING EFFECTIVE ELASTIC MODULUS OF A COMPOSITE SLICKLINE CABLE

(71) Applicant: Halliburton Energy Services, Inc., Houston, TX (US)

(72) Inventors: Hua Xia, Huffman, TX (US); Yinghui Lu, The Woodlands, TX (US); Sean Gregory Thomas, Frisco, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/909,628

(22) PCT Filed: Jan. 6, 2015

(86) PCT No.: PCT/US2015/010332
§ 371 (c)(1),
(2) Date: Feb. 2, 2016

(87) PCT Pub. No.: WO2016/111681
PCT Pub. Date: Jul. 14, 2016

(65) Prior Publication Data
US 2016/0341702 A1 Nov. 24, 2016

(51) Int. Cl.
*G01M 7/02* (2006.01)
*G01H 13/00* (2006.01)
(Continued)

(52) U.S. Cl.
CPC ............. *G01H 13/00* (2013.01); *G01L 1/10* (2013.01); *G01M 7/00* (2013.01)

(58) Field of Classification Search
CPC ............. G01M 7/00; G01L 1/10; G01H 13/00
(Continued)

(56) References Cited

U.S. PATENT DOCUMENTS 6,359,446 B1  3/2002  Little, Jr.
6,698,288 B2  3/2004  Shirzad et al.
(Continued)

FOREIGN PATENT DOCUMENTS

WO  2006/049561 A1  5/2006

OTHER PUBLICATIONS

International Search Report and Written Opinion issued in related PCT Application No. PCT/US2015/010332 mailed on Sep. 8, 2015, 10 pages.
(Continued)

*Primary Examiner* — John Chapman, Jr.
(74) *Attorney, Agent, or Firm* — Scott Richardson; Baker Botts L.L.P.

(57) ABSTRACT

In accordance with embodiments of the present disclosure, systems and methods for determining a dynamic effective elastic modulus of a composite slickline or wireline cable are provided. A system for estimating the effective elastic modulus (or change thereof) may include a sensing head assembly, a vibration generator, a pair of pulleys, and an optical-based signal processing assembly. The system may detect a resonant frequency of a section of the composite cable held between the two pulleys and estimate the effective elastic modulus based on the detected resonant frequency variation. Adjustments for weight and length of the cable extending into the wellbore may be made as well to determine the dynamic elastic modulus of the cable. The opto-mechanical integrated system described below may enable real-time elastic modulus determination. The system may provide a non-contact inspection method for monitoring mechanical fatigue of a composite cable without interfering with the composite cable intervention operation.

20 Claims, 7 Drawing Sheets

(51) Int. Cl.
*G01M 7/00* (2006.01)
*G01L 1/10* (2006.01)

(58) Field of Classification Search
USPC .................................................. 73/579, 581
See application file for complete search history.

(56) References Cited

U.S. PATENT DOCUMENTS

| | | |
|---|---|---|
| 6,838,670 B2 | 1/2005 | Lewis et al. |
| 7,080,561 B2 | 7/2006 | Bohlmann et al. |
| 7,086,285 B2 | 8/2006 | Reed |
| 7,812,616 B2 | 10/2010 | Doyen |
| 7,966,883 B2 | 6/2011 | Lorraine et al. |
| 8,286,498 B1 | 10/2012 | Robertson et al. |
| 8,380,028 B2 | 2/2013 | Kojima et al. |
| 8,393,784 B2 | 3/2013 | Ringermacher et al. |
| 8,442,301 B2 | 5/2013 | Dragovich et al. |
| 2008/0010031 A1 | 1/2008 | Kim et al. |
| 2012/0029844 A1 | 2/2012 | Haikola et al. |
| 2012/0085531 A1 | 4/2012 | Leising et al. |
| 2013/0341009 A1 | 12/2013 | Cancino et al. |
| 2014/0174727 A1 | 6/2014 | Huizer |

OTHER PUBLICATIONS

Bourkas, G. et al., "Estimation of Elastic Moduli of Particulate Composites by New Models and Comparison with Moduli Measured by Tension, Dynamic, and Ultrasonic Tests", Advances in Materials Science and Engineering, vol. 2010 13 pages.

Siddiqui, M. Z. et al., "Determination of Young's Modulus of Metallic and Composite Materials by Digital Image Correction" Journal of Space Technology, vol. 1, No. 1, Jul. 2012, pp. 32-37.

AccuScan—Diameter and Ovality Measurement Systems, http://www.betalasermike.com/index.php/en/beta-lasermike-products-en/diameter-a-ovality-en, 2 pages, (2015).

Kwaaitaal, T. et al. "Determination of Young's Modulus or Poisson's Ratio using Eddy Currents" Exp. Mech., vol. 19, No. 12, pp. 450-455, Mar. 1979.

DETERMINING EFFECTIVE ELASTIC MODULUS OF A COMPOSITE SLICKLINE CABLE

CROSS-REFERENCE TO RELATED APPLICATIONS

The present application is a U.S. National Stage Application of International Application No. PCT/US2015/010332 filed Jan. 6, 2015, which is incorporated herein by reference in its entirety for all purposes.

TECHNICAL FIELD

The present disclosure relates generally to well drilling, hydrocarbon recovery, and well intervention operations and, more particularly, to systems and methods for monitoring the mechanical strength of a wireline or slickline being moved through a wellbore.

BACKGROUND

Hydrocarbons, such as oil and gas, are commonly obtained from subterranean formations that may be located onshore or offshore. The development of subterranean operations and the processes involved in removing hydrocarbons from a subterranean formation typically involve a number of different steps such as, for example, drilling a wellbore at a desired well site, treating the wellbore to optimize production of hydrocarbons, and performing the necessary steps to produce and process the hydrocarbons from the subterranean formation.

After drilling a wellbore that intersects a subterranean hydrocarbon-bearing formation, a variety of downhole tools may be positioned in the wellbore during exploration, completion, production, and/or remedial activities. For example, temporary packers may be set in the wellbore during the completion and production operating phases of the wellbore. In addition, various operating tools including flow controllers (e.g., chokes, valves, etc.) and safety devices such as safety valves may be deployed in the wellbore. Such tools are often lowered downhole by a wireline, a work string, or a slickline and may be configured with a fishing neck to facilitate recovery at a later time. Once such downhole logging service is completed, the tool may be retrieved with the wireline, work string, or slickline.

As noted above, a slickline can be used to lower and retrieve wellbore tools from the wellbore. A slickline generally includes a metal wire based cable or nonelectric cable with a polymeric coating to protect the cable from mechanical wear during deployment and retraction from the wellbore. Recent developments in the field of slicklines have been focused on realizing greater mechanical strength through the use of composite slicklines. These slicklines are constructed from unidirectional carbon fibers suspended in a thermoplastic matrix material. Unfortunately, such carbon fiber reinforced composite slicklines can suffer from structural defects, such as carbon fiber breakage, fiber delaminating or de-bonding from the matrix, and inconsistent volumetric fractions of the carbon fibers, among others.

Such defects are often not measurable after the manufacturing process, but can grow quickly during dynamic tensile loading of the slickline during use in the field. This makes it difficult to determine if a composite slickline cable can be reused after each service. The gradual cable degradation might reduce the minimum breaking strength of the cable during downhole tool logging services. Furthermore, corrosion caused by exposure to fluids in the borehole, bending or kinking, and insufficient or excessive torque also can degrade the mechanical strength of a slickline cable so that the maximum allowable tool-string weight has to be reduced. Accordingly, it is desirable to inspect a composite slickline cable before or after each field logging service to avoid undesirable effects that may require additional service for fishing a lost tool-string from the bottom of the wellbore.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

Illustrative embodiments of the present disclosure are described in detail herein. In the interest of clarity, not all features of an actual implementation are described in this specification. It will of course be appreciated that in the development of any such actual embodiment, numerous implementation specific decisions must be made to achieve developers' specific goals, such as compliance with system related and business related constraints, which will vary from one implementation to another. Moreover, it will be appreciated that such a development effort might be complex and time consuming, but would nevertheless be a routine undertaking for those of ordinary skill in the art having the benefit of the present disclosure. Furthermore, in no way should the following examples be read to limit, or define, the scope of the disclosure.

Certain embodiments according to the present disclosure may be directed to systems and methods for determining a dynamic effective elastic modulus of a composite slickline or wireline cable. The effective elastic modulus of such composite cables depends strongly upon intrinsic structural defects that may be created in the composite material during the manufacturing process. Extrinsically, these structural defects may grow rapidly in response to dynamic tensile loading stresses on the composite cable, and these defects may lead to a reduction of the effective elastic modulus and tensile loading capability of the cable. This may lead to undesirable effects on the cable when dynamic loading tensile stress exceeds the 50% cable minimum breaking strength threshold. The tension measurement from the composite cable may not be used on its own to determine when these effects might take place, because the effective elastic modulus of the composite cable may change as a result of growing structural defects in the cable.

Existing techniques for determining elastic modulus of composites often entails performing measurements in a laboratory prior to deployment of the cable into the field. However, this approach cannot be used to provide a measurement of dynamic effective elastic modulus of the cable while it is being used in the field during downhole logging service operations. Attempts at providing elastic modulus measurements in the field have used X-ray measurements and ultrasonic probes. Unfortunately, the X-ray measurements are typically directed to just one area of scanning along the cable, and the contrast available through the X-ray sensors may not be high enough to detect the defects in the composite cable. Ultrasonic probe measurements often require the probe to be in contact with the composite material, but this sort of contact-sensing cannot be used while the composite cable is actively being run downhole. Other techniques for determining stationary elastic modulus may only detect the mechanical state of the composite cable at a single point along the cable, instead of providing information related to the state of the entire composite cable.

To address these drawbacks, the disclosed system for estimating effective elastic modulus (or change thereof) may include a sensing head assembly, a vibration generator, a pair of pulleys, and an optical-based signal processing assembly. As described in detail below, the system may detect a natural resonant frequency of a section of the composite cable held between the two pulleys and estimate the effective elastic modulus based on the detected resonant frequency. Adjustments for the weight and length of the cable extending into the wellbore may be made as well to determine the dynamic elastic modulus of the entire cable. The opto-mechanical integrated system described below may enable real-time elastic modulus determination. In addition, the system may provide a nondestructive, non-contact inspection method for monitoring a mechanical fatigue trend of the composite cable without interfering with the composite cable logging service operation.

In the disclosed techniques, the non-contact elastic modulus measurement may enable an analysis of internal structural defects in the cable, without using electromagnetic waves or microscopic techniques. As a result, the disclosed techniques may be performed at a field location while the cable is being used to perform a logging service process. The disclosed systems and methods may simplify real-time in-situ cable mechanical fatigue inspections in the field for preventing undesirable wear on the cable during downhole tool intervention operations. The techniques disclosed herein may be equally applied to other types of cables, such as metal, composite, or mixed metal-composite cables, in situations where the cable mechanical fatigue is a concern.

Figure 1:
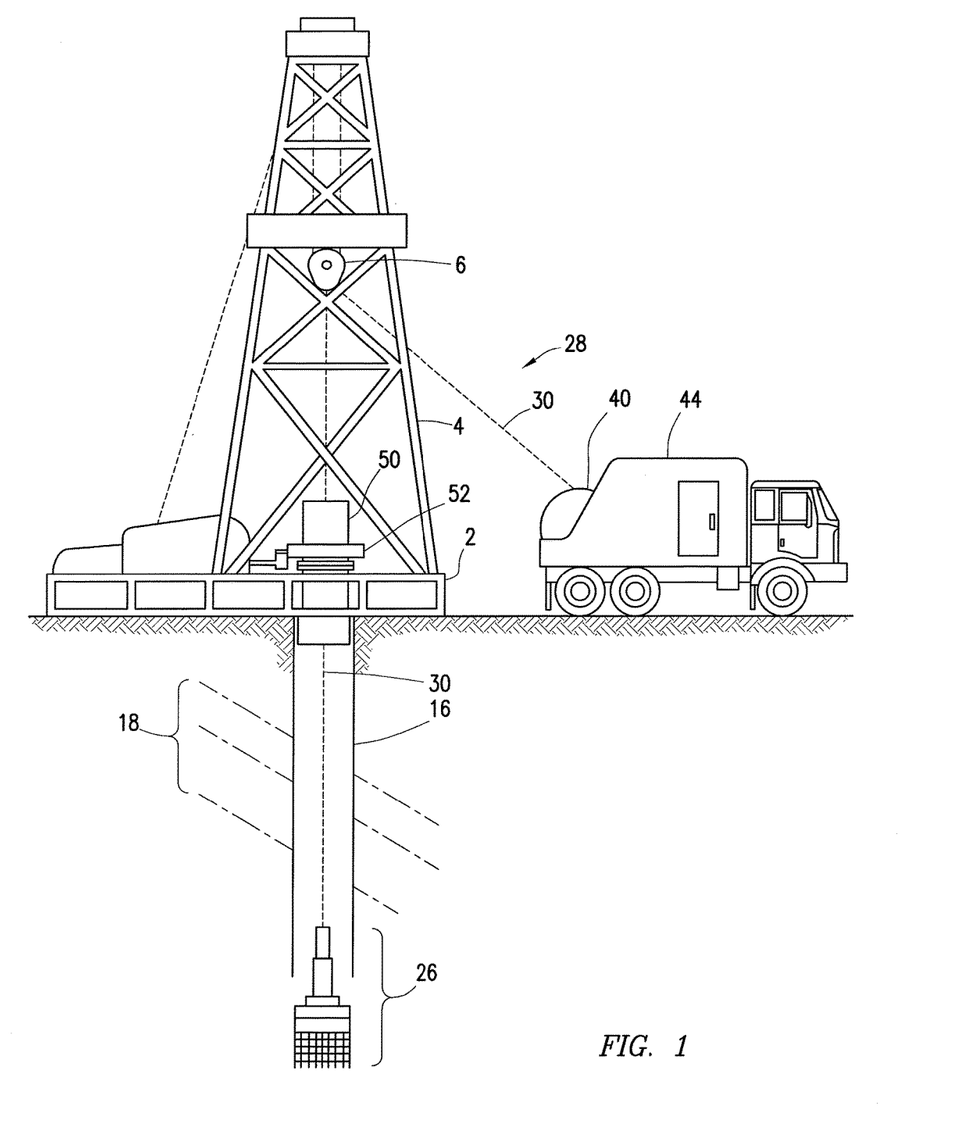
FIG. 1 is a schematic partial cross-sectional view of a slickline being deployed in a wellbore drilling environment, in accordance with an embodiment of the present disclosure.

Turning now to the drawings, FIG. 1 illustrates oil well equipment being used in an illustrative drilling environment. A drilling platform 2 supports a derrick 4 having a traveling block 6 for raising and lowering a drill string (not shown). The drill string creates a wellbore 16 that passes through various formations 18. At various times during the drilling process, the drill string may be removed from the wellbore 16. Once the drill string has been removed, a subsurface device 26 (e.g., a plug, packer, etc.) may be lowered downhole to the desired setting depth via a conveying member 28. The subsurface device 26 may be used, for example, to seal off or isolate zones inside the wellbore 16. When the subsurface device 26 reaches the desired location within the wellbore 16, the subsurface device 26 is set in place within the wellbore 16. After the subsurface device 26 is securely set in place, the conveying member 28 may be retracted.

In present embodiments, the conveying member 28 includes a composite slickline cable 30, which is a nonelectric cable made from a carbon fiber reinforced polymer material with a protective polymeric coating sheath. In other embodiments, the conveying member 28 may include a composite wireline cable that includes one or more communication lines surrounded by a carbon fiber reinforced polymer material with a protective coating sheath. It should be noted that other materials, such as fiberglass, ceramic fiber, and metal fibers, may be used to provide the reinforcement within the composite cable 30. The slickline cable 30 may be unspooled from a spool 40 on a slickline truck 44 onto a sheave (e.g., traveling block 6 or some other sheave) on the drilling platform 2. From here, the slickline cable 30 with the tool-string (26) may be lowered (deployed) into the wellbore 16 and subsequently raised (retracted) from the wellbore 16 after placing the tool-string or subsurface device 26 as described above. A tool-string (26) may be sonic tool, or formation analyzer, or a combination of gamma-ray, resistivity, and neutron sensing devices.

In presently disclosed embodiments, an elastic modulus measuring system 50 may be disposed above a wellhead 52 positioned at the top of the wellbore 16. The elastic modulus measuring system 50, as described in detail below, may be used to detect a frequency of oscillation of a section of the composite slickline cable 30 disposed within the elastic modulus measuring system 50, in order to estimate the effective elastic modulus of that section of the composite slickline cable 30. Hereinafter the term "sectional composite slickline cable" may be used to refer to this section of the composite slickline cable 30. The elastic modulus measuring system 50 may be integrated with existing slickline/wireline logging tools, in order to provide monitoring and diagnosis of composite slickline cable operation/health without interfering with the operation of the composite slickline cable 30.

Figure 2:
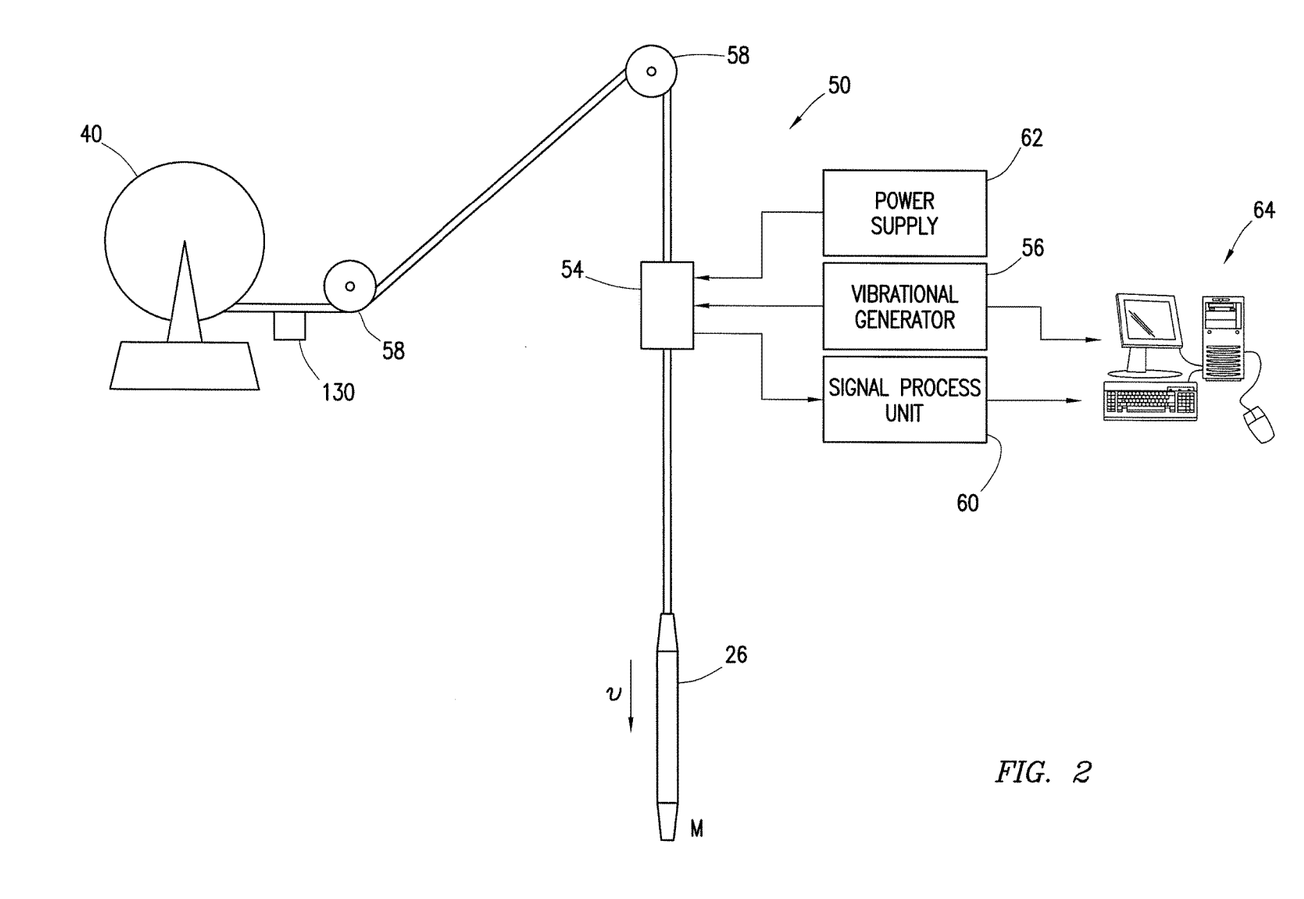
FIG. 2 is a schematic representation of a system for analyzing the effective elastic modulus of the slickline of FIG. 1, in accordance with an embodiment of the present disclosure.

FIG. 2 illustrates the elastic modulus measuring system 50 in greater detail. The elastic modulus measuring system 50 may include a sensing head assembly 54, a vibration generator 56, one or more pulleys 58, and an optical based signal processing unit 60. FIG. 2 depicts the main opto-mechanic parts and sub-systems that may be integrated together as an analytical instrument for installation in the wellhead. The elastic modulus measuring system 50 may be used for scanning an elastic modulus of a composite slickline cable 30 while the composite slickline cable 30 is in transient operation (i.e., being lowered or raised relative to the wellhead 52).

As mentioned above, the composite slickline cable 30 may be wrapped on a cable spool 40 set on a truck or other suitable base. The composite slickline cable 30 may be connected to the subsurface device 26 or tool. This subsurface device 26 may include, for example, a multi-sensor assembly, a sonic device, a gamma-ray and neutron irradiation sensing assembly, and so forth. The composite cable 30 may travel to the top pulley (e.g., sheave) 58 and pass from the top pulley 58 through a wellhead assembly (e.g., Christmas tree) to an open-hole or cased wellbore (e.g., 16 of FIG.

1). The tool-string or subsurface device 26 may have a weight of approximately M and move with a downward velocity v, as illustrated.

The elastic modulus measuring system 50 may include a power supply 62, a vibration generator 56, and a signal processing unit 60 that provide electric and mechanical support to sensing at the wellhead. With these components, the elastic modulus measuring system 50 may perform interrogations, measurements, and log updates, as well as generate alarms and reports as needed. The power supply 62 may provide power for operating the mechanical and sensing components of the sensing head assembly 54. The vibration generator 56 may provide control signals for operating the sensing head assembly 54 to vibrate the composite cable 30 at a desired frequency as the cable moves through the sensing head assembly 54. The signal processing unit 60 may process signals received from the sensing head assembly 54 to determine an effective elastic modulus of the composite slickline cable 30 moving through the sensing head assembly 54.

The elastic modulus measuring system 50 may interface directly or wirelessly via remote database access to a supervisory control and data acquisition (SCADA) system 64. In some embodiments, the SCADA may be located on another part of the rig platform. It should be noted that, in some embodiments, one or more of the power supply 62, the vibration generator 56, and the signal processing unit 60 may be packaged within the sensing head assembly 54. In other embodiments, these components may be disposed outside of and interface directly with the sensing head assembly 54.

Figure 3:
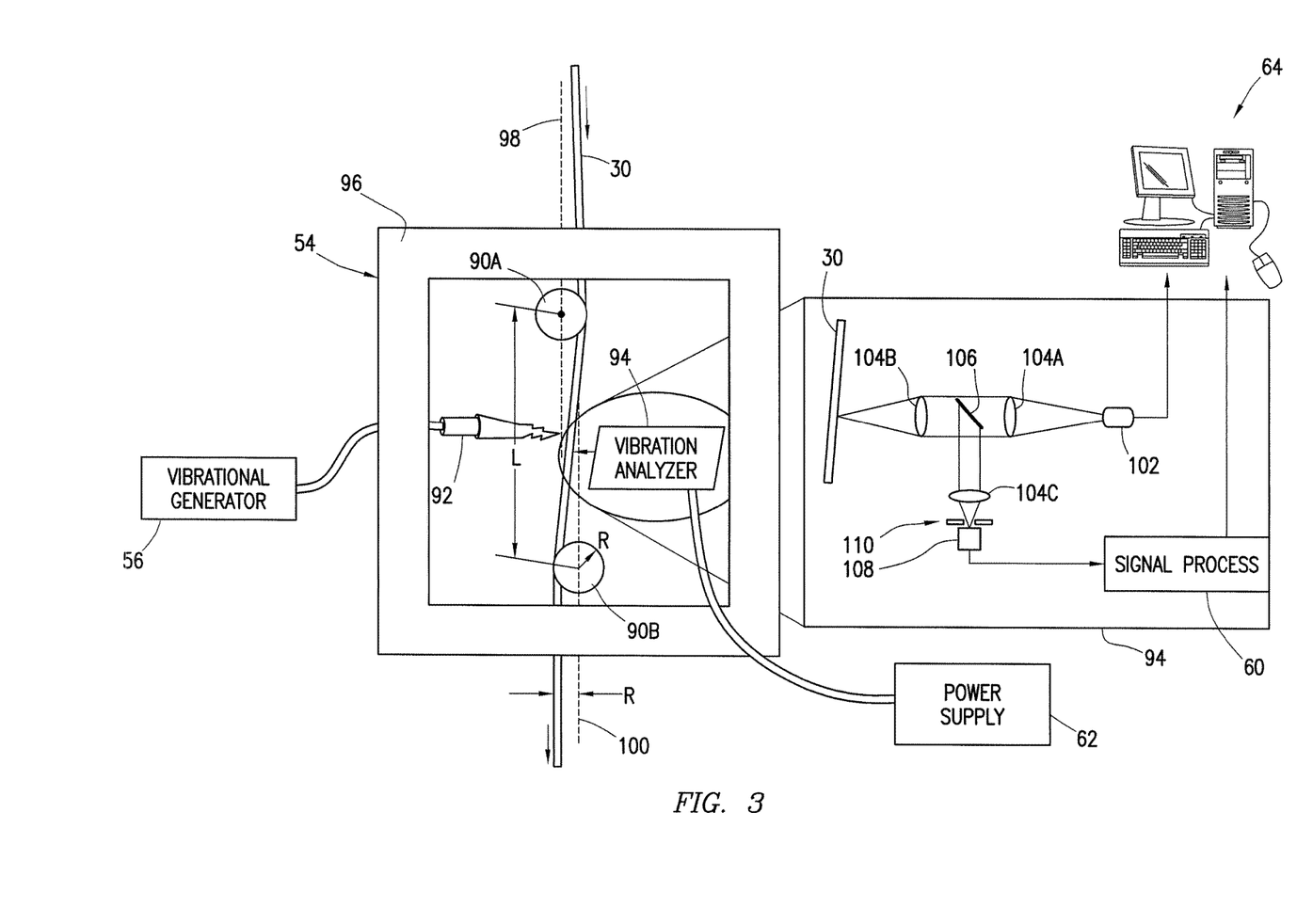
FIG. 3 is a schematic representation of a sensing head assembly used in the analysis system of FIG. 2, in accordance with an embodiment of the present disclosure.

FIG. 3 is a more detailed schematic diagram illustrating the elastic modulus measuring system 50. The detailed sensing head assembly 54 may include a pair of pulleys 90A and 90B, a vibration generator component 92, and a vibration analyzer 94, all contained within a housing 96. As described in detail below, the elastic modulus measuring system 50 may provide a non-contact elastic property analysis method for evaluating a mechanical degradation trend of the composite slickline cable 30.

The pulleys 90 may feature wheels designed to rotate freely with the composite slickline cable 30 as the cable is moved through the sensing head assembly 54. In the illustrated embodiment, the center of the upper pulley 90A and the left edge of the bottom pulley 90B may be aligned with each other along a vertical line 98, while the composite slickline cable 30 passes between the two pulleys 90. Similarly, the right edge of the upper pulley 90A and the center of the lower pulley 90B may be aligned with each other along a vertical line 100 that is a distance R (i.e., radius of the pulleys 90) from the vertical line 98. However, in other embodiments, the pulleys 90 may be aligned with respect to each other in different ways. Due to the weight of the subsurface device or tool pulling on the composite slickline cable 30, the sectional composite slickline cable 30 may be tensed across the two pulleys 90 while still being able to smoothly pass the pulleys 90 during downhole loading operations.

The vibration generator component 92 disposed inside the illustrated housing 96 may be part of the overall vibration generator 56 described above. The vibration generator 56 may be used to provide a modulated and controllable signal to the vibration generator component 92 for generating a vibration signal to excite the sectional composite slickline cable 30 into transient vibration. That is, the vibration generator 56 may output a signal to the vibration generator component 92, and the vibration generator component 92 causes the composite cable 30 to vibrate according to the received signal.

In presently disclosed embodiments, the vibration generator component 92 may cause the composite cable 30 to vibrate without coming into direct contact with the composite slickline cable 30. This may prevent undesirable impact forces (e.g., friction, shearing, etc.) from being applied to the sectional cable 30. To that end, in the illustrated embodiment, the vibration generator component 92 may include a high-pressure gas (e.g., air, nitrogen, argon, etc.) gun nozzle used to excite the composite cable 30. The gun nozzle may output the inert gas or air at a controlled frequency to cause the composite cable 30 to vibrate between the pulleys 90.

In other embodiments, the vibration generator component 92 may include a water gun that operates similarly to the illustrated air gun. In still other embodiments, the vibration generator component 92 may include a piezoelectric based electro-mechanical shaker that is used to excite the composite slickline cable 30 for transient vibration. In such instances, the piezoelectric shaker may be coupled to the upper pulley 90A or the lower pulley 90B to cause the composite slickline cable 30 to oscillate without directly contacting the composite slickline cable 30. By not touching the cable, the piezoelectric motor may not apply any undesirable friction forces to the composite slickline cable 30 moving through the sensing head assembly 54.

The vibration analyzer 94 may include an optical based vibration signal analysis assembly disposed in the housing 96 of the sensing head assembly 54. The vibration analyzer 94 may include, for example, a laser source 102, lenses 104, a filter 106, a photo-detector 108, and the signal processing unit 60. The laser source 102 may output a laser light that is directed to the composite cable 30 by a collimating lens 104A and a focus lens 104B. The filter 106 may include a dichromic filter designed to selectively pass certain colors of light from the laser source 102 toward the composite slickline cable 30, while reflecting other colors of light from the composite slickline cable 30 through another focus lens 104D and ultimately to the photo-detector 108.

In some embodiments, the vibration analyzer 94 may be constructed by adapting components of a commercially available optical system typically used for cable diameter analysis. This may enable a relatively simple assembly process for the vibration analyzer 94. Such available optical systems may already be configured for use in a wellbore environment and constructed in a size and shape appropriate for installation on a wellhead.

In the illustrated embodiment, the vibration analyzer 94 may include a pinhole 110 fixed between the focus lens 104C and the photo-detector 108, in order to provide a higher sensitivity vibration detection. The pinhole 110 may only allow light in when the light hits a desired focal point, giving a more sensitive measurement than systems where the light does not have to be focused to a point. The pinhole 110 may be sized to approximately 50 to 100 micrometers in diameter.

In present embodiments, the vibration analyzer 94 may serve to provide non-contact measurements of the resonant frequency of the sectional composite slickline cable 30. Thus, the opto-mechanical integrated sensing head assembly 54 may provide a nondestructive inspection method for monitoring the mechanical fatigue on the composite slickline cable 30 without interfering with the slickline-mounted tool logging service. Existing systems used to determine fatigue and wear on such slicklines and wirelines often utilize contact sensors that can apply undesirable forces to the cable and/or require that the cable remain unmoving during measurements. Instead, the disclosed embodiments offer a measurement system 50 capable of estimating an effective elastic modulus of the composite slickline cable 30 while the composite cable 30 is being run in or out of the wellbore.

The signal processing unit 60 may receive a time-domain power signal from the photo-detector 108 representing the light reflected off the vibrating composite slickline cable 30. The signal processing unit 60 may analyze the time-domain power signal using a fast Fourier transform algorithm to determine a resonant frequency of the sectional composite slickline cable 30 in the sensing head assembly 54. The fast Fourier transform algorithm may involve analyzing the received vibration signal in the frequency domain to locate a frequency at which the signal peaks in the frequency domain. This determined resonant frequency of the sectional composite slickline cable 30 may shift in response to a loss of the effective elastic modulus of the cable. In addition, the resonant frequency may also shift in response to a change in total length and/or weight of the composite slickline cable 30 (and supported subsurface tool) within the wellbore.

As mentioned above, the detected resonant frequency of the sectional composite cable 30 may be used to estimate an effective elastic modulus ($E_{eff}$) of the composite slickline cable 30. The effective elastic modulus is a property that may be used to describe and/or predict the deformation behavior of a composite polymer material (e.g., material of the composite cable 30) under loading. The relationship between the stress and strain of the composite polymer material is often defined by the effective elastic modulus (or Young's modulus). The ability of the composite polymer material to resist loading may depend on the effective elastic modulus of the composite polymer material.

The materials that make up the composite slickline cable 30 may include carbon fiber reinforcements and a polymeric matrix material, and these materials may each deform differently when loads are applied thereto. In the composite polymer material, the polymeric matrix is relied on for providing load transfer through the composite slickline cable 30, while the carbon fiber reinforcements are relied on for carrying the load on the composite slickline cable 30 (e.g., from a subsurface device and the weight of the cable 30). The $E_{eff}$ of the composite material is generally considered to be an average of both the elastic modulus of the polymeric matrix plastic and the elastic modulus of the embedded carbon fibers.

As illustrated in FIG. 3, a sectional composite slickline cable 30 of length L may pass through the pair of pulleys 90 with a slight shift horizontally from one pulley 90A to the next 90B. However, this shift may be negligible compared to the length L and the amount of tension on the sectional cable 30 is assumed to be entirely in a vertically downward direction. The subsurface tool being carried by the composite cable 30 may induce tension in the composite slickline cable 30 according to the below equation 1, where r represents a radius of the composite slickline cable 30, g represents a gravity constant, and M represents the mass of the tool-string being supported by the composite slickline cable 30.

$$\sigma_{tool} = \frac{Mg}{\pi r^2} \quad (1)$$

In general, the weight of the tool-string or subsurface tool can be reduced due to the buoyancy of the tool-string in borehole fluid. This decrease in weight may depend upon a weight difference of the tool-string in air and in the borehole fluid. For simplicity, this buoyance effect is omitted in the following discussion.

In addition, the weight of the slickline cable 30 disposed in the wellbore may induce additional tension in the sectional composite cable. Thus, during downhole tool logging services, the dynamic tension in the composite cable 30 may depend on a length of the composite slickline cable 30 disposed in the wellbore. The total composite slickline cable tension may therefore be expressed according to the following equation 2. In this equation, the variable $\rho$ represents a density of the composite cable 30 and z(t) represents the length of the composite slickline cable 30 at downhole depth z and time t.

$$\sigma(z,t) = \sigma_{tool} + \sigma_{cable} = \frac{[M \cdot g + \pi r^2 \cdot \rho \cdot z(t)]}{\pi r^2} \quad (2)$$

In some embodiments, a tension meter or tension sensor 130 may be disposed in the elastic modulus measurement system 50 of FIG. 2 to detect this dynamic tension. For example, as illustrated, the tension sensor 130 may be positioned immediately after the cable spool 40. Such sensors 130 are typically used to measure a dynamic tension in the composite slickline cable 30, in order to monitor and ensure that the cable tension is maintained within a desired operating range, or less than 50% minimum breaking strength. In embodiments that do not include a tension sensor, the tension may be calculated according to equation 2 above based on the mass of the tool-string or subsurface tool 26, the radius and density of the slickline cable 30, and a length of the slickline cable 30 that is unwound from the spool 40 at a given time t.

A relatively simple estimate for the maximum tensile strength of the composite slickline cable 30 is based on the assumption that cable failure is based on a volumetric average of the mechanical strength of the plastic matrix material and the mechanical strength of the carbon fibers. An expression of this estimated maximum axial strength of the composite slickline cable 30 is provided below in equation 3. In this equation, $E_m$ and $E_{cf}$ represent the elastic modulus of the plastic matrix material and the carbon fiber, respectively. The variable $\epsilon_b$ represents the minimum breaking strain of the composite slickline cable 30, $f_m$ represents the volumetric fraction of the thermoplastic matrix material, and $1-f_m$ represents the corresponding volumetric fraction of the carbon fibers in the composite slickline cable 30.

$$\alpha_{axial} = [f_m * E_m + (1-f_m) * E_{cf}] \cdot \epsilon_b = E_{eff}(\text{axial}) \cdot \epsilon_b \quad (3)$$

The maximum radial strength of the composite slickline cable may be expressed according to equation 4.

$$\sigma_{radial} = \left[ f_m * \left(\frac{1}{E_m}\right) + (1-f_m) * \left(\frac{1}{E_{cf}}\right) \right] \cdot \epsilon_b = E_{eff}(\text{radial}) \cdot \epsilon_b, \quad (4)$$

The volumetric averaged elastic modulus of equation 3 and 4 may be approximately valid under low stress conditions. However, the effective elastic modulus of the composite cable 30 may be more dominated by the volumetric percentage of the carbon fibers when all the carbon fibers are appropriately bonded with the polymer matrix material. In fact, the difference in coefficients of thermal expansion between the polymer matrix and carbon fibers may be a primary reason for the creation of the structural defects in the composite slickline cable 30 at elevated temperature because of the loss of the bonding. In this case, the polymer matrix may no longer effectively transfer external loading to the carbon fibers that are used to effectively reduce the minimum breaking strength of the composite slickline cable 30. The creation of structural defects inside the plastic matrix material by debonding carbon fibers with the polymer matrix is generally an irreversible process that effectively reduces $E_{\it eff}$ through the mechanism of plastic deformation. In addition, carbon fiber breakages caused by bending or kinking of the composite slickline cable 30 may adversely affect the minimum breaking strength of the composite slickline cable 30.

Presently disclosed embodiments offer a method for estimating the effective elastic modulus of the composite slickline cable 30 in a way that accounts for the plastic deformations that may occur within the composite material under high stress conditions and throughout the lifetime of the composite slickline cable 30. Specifically, the disclosed embodiments introduce a method for approximating the effective elastic modulus ($E_{\it eff}$) of the composite slickline cable 30 based on vibrational frequencies of the composite slickline cable 30 in the sensing head assembly 54 of FIGS. 2 and 3. In order to detect the effective elastic modulus of the slickline cable, the vibration of the sectional slickline cable is produced by a pair of pulleys 90, where the sensing head assembly 54 may excite the sectional composite slickline cable 30 using an externally modulated signal from the vibration generator 56 that causes the sectional composite slickline cable 30 to vibrate in quasi-standing wave modes.

Figure 4A:
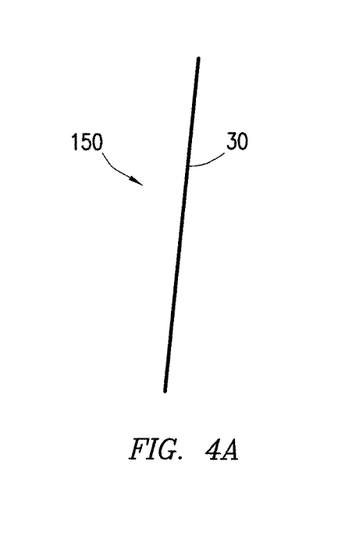
FIGS. 4A-4D provide a schematic representation of a slickline vibrating in different vibration modes for analysis, in accordance with an embodiment of the present disclosure.
Figure 4B:
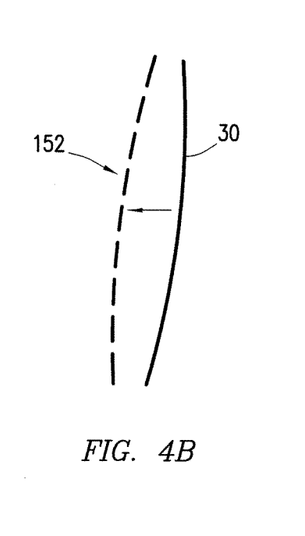
Figure 4C:
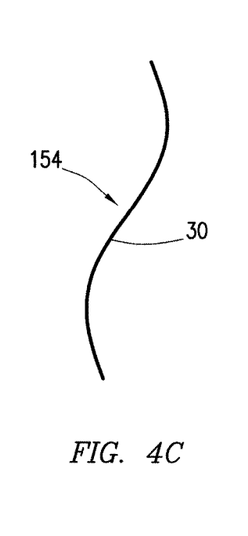
Figure 4D:
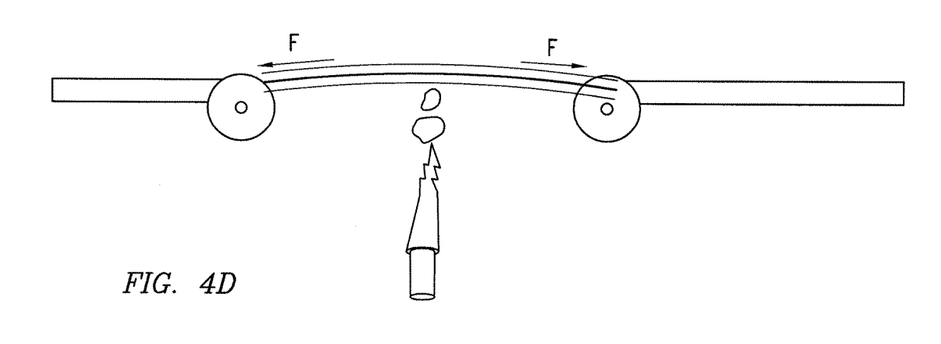

FIGS. 4A-4C illustrate three such quasi-standing wave modes of the sectional composite slickline cable 30 disposed between the pulleys 90. FIG. 4A illustrates the composite slickline cable 30 in a static state 150, such that the composite slickline cable 30 is not vibrating at all. FIG. 4B illustrates the composite cable 30 vibrating in a fundamental vibration mode 152, and FIG. 4C illustrates the composite slickline cable 30 vibrating in a first high-order vibration mode 154. Of these different modes, the fundamental frequency mode 152 may be particularly well suited for use with the setup of the composite slickline cable 30 between the two pulleys 90, as shown in FIG. 4D. The fundamental mode may be used as an effective resonator structure that enables the sectional composite slickline cable 30 disposed between the paired pulleys 90 to undergo lateral (e.g., horizontal) displacement due to excitation from a modulated driving force F. This modulated driving force F may come from the vibration generator component 92, such as a pressure gas nozzle operating according to a signal control unit.

In the setup described herein, the sectional composite slickline cable 30 may vibrate while being held under vertical tension in the amount of approximately $\sigma_\| = \pm 2F_\|$. This force $2F_\|$ and the resulting tension are in the vertical direction that is substantially perpendicular to the direction of the gas nozzle 92. The weight of the tool-string or subsurface device and cable downhole may provide enough vertical tension to the cable so that the sectional composite slickline cable 30 stretched across the two pulleys 90 acts as a resonator structure.

For the fundamental mode vibration shown in FIG. 4D, the sectional composite slickline cable 30 may have an axial (i.e., approximately vertical) displacement due to the subsurface device moving upward or downward through the wellbore. The sectional composite slickline cable 30 may also exhibit a radial displacement due to the external vibration excitation by the vibration generator component 92. By controlling a driving force output from the vibration generator component 92, the radial displacement of the composite slickline cable 30 may be limited to a vibrational amplitude of approximately 20 to 100 micrometers across the pulleys 90. Since this lateral excitation of the composite slickline cable 30 is accomplished without directly contacting the composite slickline cable 30, the sectional composite slickline cable 30 between the two pulleys 90 may be constructed as a resonator having a resonant frequency determined according to the following equation 5. In this equation, the resonant frequency may depend upon a varied tension that is affected by the weight of the composite slickline cable 30 positioned downhole at a given time, as discussed above with reference to equations 2, 3 and 4. The initial resonant frequency f(0) refers to the resonant frequency of the composite cable 30 when none of the cable extends into the wellbore.

$$f(z) = \left(\frac{1}{2\pi L}\right)\left(\frac{E_{\it eff}(\text{axial})}{\rho}\right)^{\frac{1}{2}} * \left(1 + \frac{\rho \pi r^2 z}{2M}\right) = f(0) * \left(1 + \frac{\rho \pi r^2 z}{2M}\right) \quad (5)$$

As shown herein, the effective elastic modulus of the composite slickline cable 30 may have a direct influence on the resonant frequency of the sectional composite slickline cable 30 throughout downhole well servicing operations using the cable. Thus, the detected resonant frequency of the sectional slickline cable 30 may serve as a direct indicator of changes in the effective elastic modulus and, therefore, mechanical fatigue experienced by the composite slickline cable 30 throughout its use. The measured resonant frequency may be used to visualize and log a composite cable degradation trend, as well as to predict impending failure events that may occur along the composite slickline cable 30.

Using the equations described above, the disclosed signal processing unit 60 may receive signals from the photodetector indicating the vibration of the sectional composite slickline cable 30 as a function of time. The signal processing unit 60 may determine the power spectral density of the received signal using a fast Fourier transform algorithm. This may allow the signal processing unit 60 to monitor frequency response characteristics of the cable vibration during downhole tool logging operations. Shifts in the frequency of the cable vibration may then be utilized as a sensing parameter during composite cable reliability checks, as discussed below.

Figure 5:
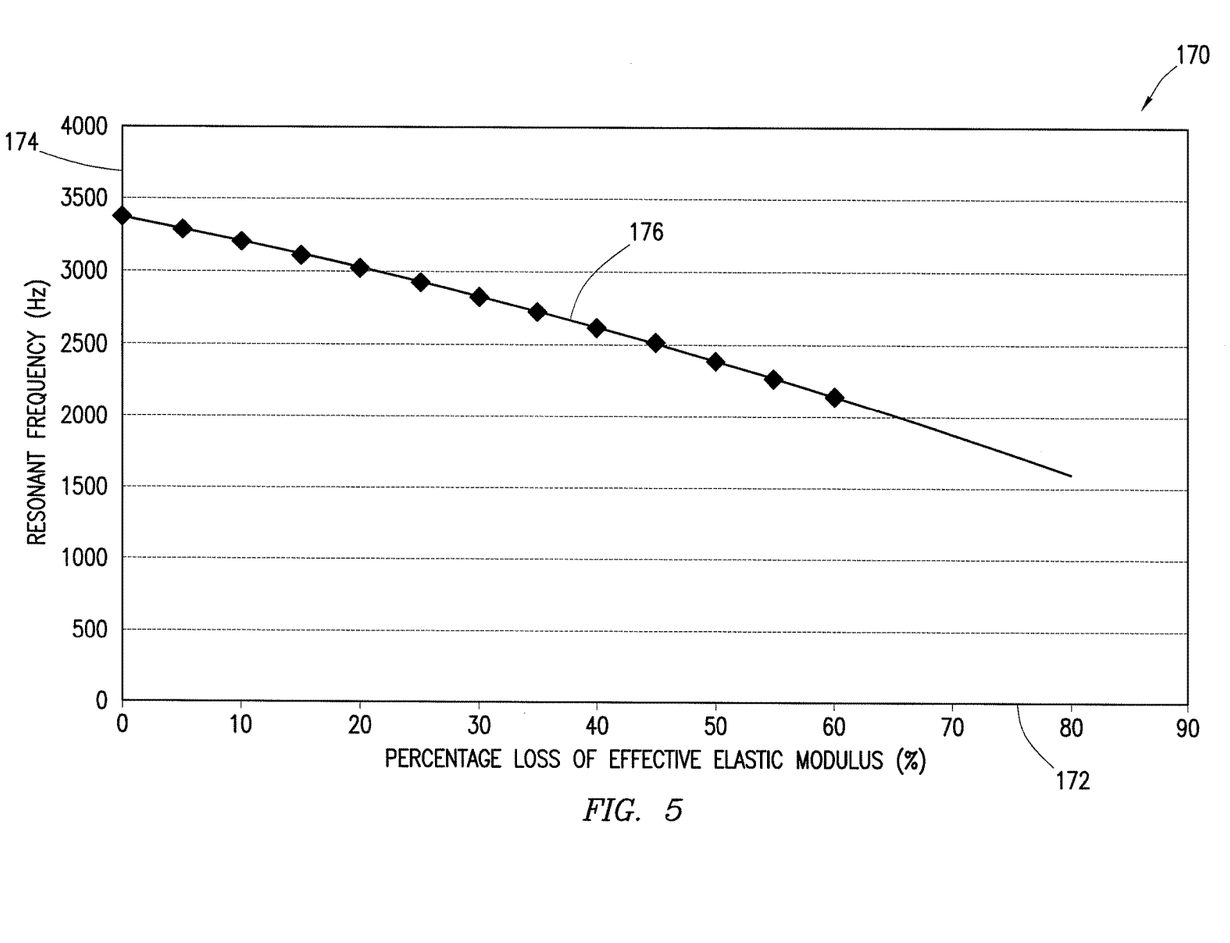
FIG. 5 is a plot illustrating a relationship between a resonant frequency and a percentage loss of effective elastic modulus of a slickline, in accordance with an embodiment of the present disclosure.

Assuming that the volumetric fraction of the plastic matrix material in the composite slickline cable 30 is low, the measured resonant frequency determined by the signal processing unit 60 may primarily depend upon the effective elastic modulus of the carbon fibers in the composite slickline cable 30. Thus, as the carbon fibers break within the composite slickline cable 30, the measured resonant frequency may shift throughout use of the composite cable 30. FIG. 5 is a plot 170 showing the effect of such elastic modulus degradation 172 on a measured resonant frequency 174 of the composite cable as the cable suffers from progressive fiber breakage. The plot 170 also includes a trend line 176 estimated from the various resonant frequency measurements taken as the effective elastic modulus 172 decreases. The trend line 176 indicates an inverse relationship between $E_{\mathit{eff}}$ degradation and the detected resonant frequency of the cable. The trend line 176 may be expressed according to the following transfer function of equation 5. It should be noted that other trend line equations may be determined corresponding to the operation of other composite cables.

$$f(E_{\mathit{eff}}) = 3370.8 - 15.924 * \xi - 0.0765 * \xi^2 \qquad (6)$$

In this equation, $\xi$ may represent a percentage loss 172 of the composite cable elastic modulus $E_{\mathit{eff}}$(axial). For these measurements, the initial resonant frequency may be based on a section length L of the composite cable equal to approximately 0.5 meters across the two pulleys. Other lengths of the sectional cable may be used in other embodiments. The downward progression of the resonant frequency 174 (as shown in the trend line 176) may occur when the collective effect of carbon fiber breakage, delamination, de-bonding, or cracking in the cable reaches a point where it is no longer negligible. The downward progression of the resonant frequency 174 may be particularly pronounced when the composite cable is experiencing either high dynamic loading stresses or high strain rate loading.

Figure 6:
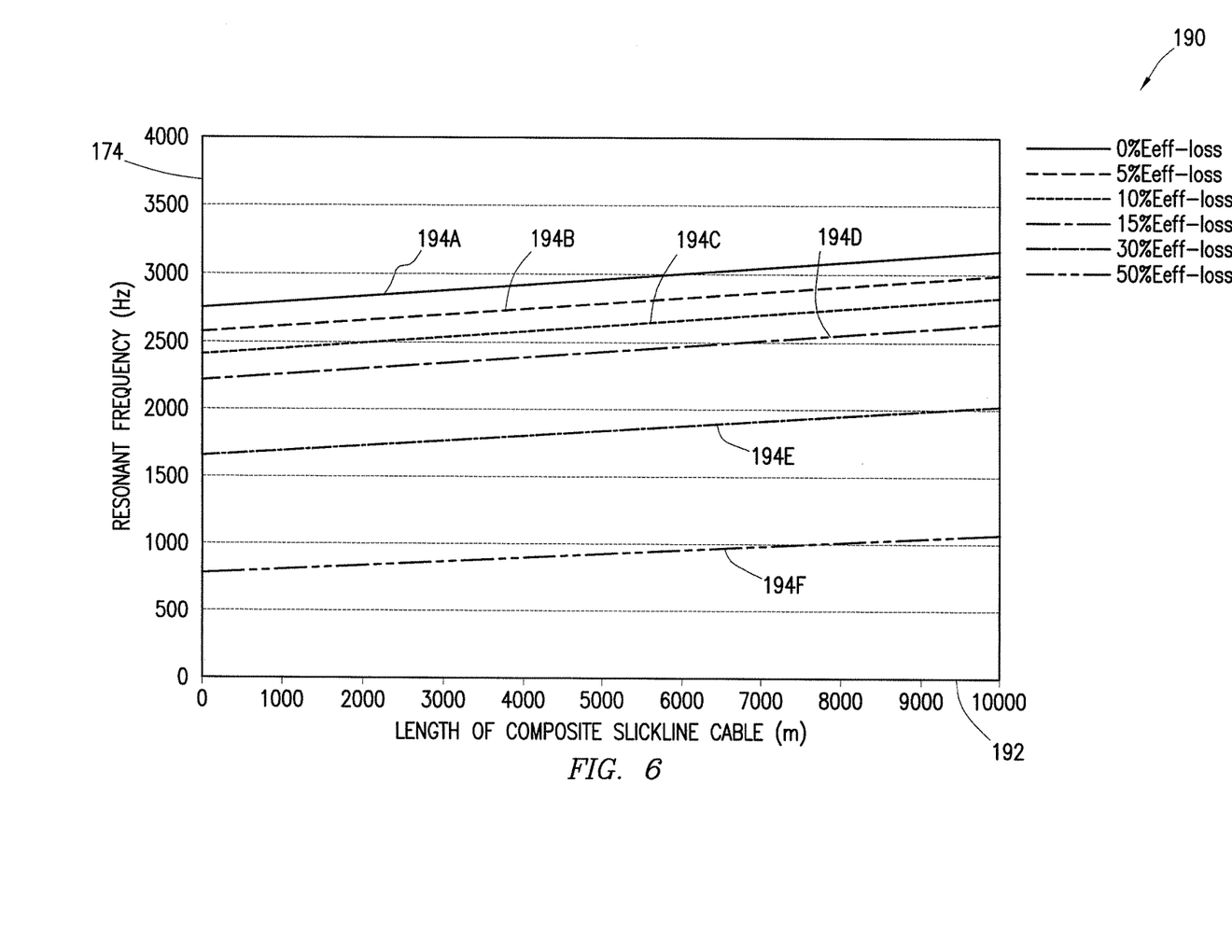
FIG. 6 is a plot illustrating a relationship between a length of composite slickline to resonant frequency for slicklines having different percentage loss of effective modulus, in accordance with an embodiment of the present disclosure.

FIG. 6 is another plot 190, this one illustrating the effect of a length 192 of the composite cable disposed in the wellbore on the resonant frequency 174 measured by the sensing head assembly. Multiple curves 194 are illustrated, each representing a different percentage loss (172) of $E_{\mathit{eff}}$ (axial). The top curve 194A may correspond to an initial cable status that has a frequency response of around approximately 3.39 kilohertz (kHz) at negligible cable weight and cable length. When the downhole tool is positioned in the wellbore at a depth of approximately 10,000 meters, however, this increase in length may add up to approximately 3,000 pounds of extra cable weight for the cable to support. This increase in weight may upshift the resonant frequency of the sectional composite cable by approximately 200 Hz to reach 3.59 kHz, as illustrated.

As illustrated, increased degradation of the composite cable may result in a lower resonant frequency of the cable when compared to another cable of the same length with a higher effective elastic modulus. For example, the resonant frequency at the starting point (i.e., negligible cable weight and cable length) of the illustrated second curve 194B is lower than the resonant frequency at the starting point of the first curve 194A. However, the slope of each respective curve 194 may be approximately the same, as the resonant frequency 174 increases as the cable weight and length increase.

The loss of the effective elastic modulus between different curves 194 may significantly affect the resonant frequency 174 detected by the sensing head assembly. For example, the resonant frequency 174 may downshift from the original 3.39 kHz to 2.39 kHz with a 50% reduction in effective elastic modulus, as determined by comparing the curves 194A and 194F of FIG. 6. Such a downshift in the resonant frequency 174 may be relatively easily detected and analyzed by the signal processing unit by using a fast Fourier transform algorithm and converting the resonant frequency to a relative elastic modulus loss percentage.

The signal processing unit 60 of FIGS. 2 and 3 may be equipped to estimate the effective elastic modulus of the composite slickline cable 30 based on the resonant frequency of the sectional cable detected via the vibration analyzer 94. More specifically, the signal processing unit 60 may utilize a calibrated look-up table or other calibration model to determine the loss percentage of the cable elastic modulus based on the detected resonant frequency. In some embodiments, the signal processing unit may utilize a calibration model to estimate the effective elastic modulus based on the detected resonant frequency and the cable tension (due to the tool-string or subsurface device 26 and/or the downhole cable weight).

The elastic modulus measuring system 50 may be calibrated using laboratory testing processes. In some embodiments, the laboratory tests may include taking stress-strain measurements of different samples of carbon fiber reinforced composite cables. These different samples may include different relative percentage losses of effective elastic modulus. This may be accomplished by using several artificially damaged composite cable samples, each having a different percentage of broken carbon fibers embedded in the respective polymeric matrix. The resulting stress-strain measurements may be used to determine an effective elastic modulus, maximum stress, breaking strain, yield points, and plastic points for each of the samples. The linear slope of the stress-strain curve corresponds to the effective elastic modulus of a given sample.

The calibration also involves detecting the resonant frequency for each of the samples, for example by using the vibration analyzer 94. A direct correlation may then be determined between the measured resonant frequency and the loss of effective elastic modulus based on the tested samples. For example, a transfer function (similar to equation 5 above) may be determined to describe the effect of the percentage $E_{\mathit{eff}}$(axial) loss on the resonant frequency detected via the vibration analyzer 94.

The relationship between effective elastic modulus and resonant frequency may also be adjusted based on changes in the length and/or weight of the cable positioned downhole. As discussed above with respect to FIG. 6, the changing length of the downhole cable may have approximately the same effect on the resonant frequency for any of the samples, no matter what their respective percentage loss of $E_{\mathit{eff}}$(axial). Thus, the calibration model may be updated to factor in the increase of resonant frequency with the length of the composite slickline cable 30. The length may be measured directly using a sensor on the spool 40, or the length and/or weight factor may be determined based on a sensed tension (e.g., via 130) on the composite cable 30.

In addition to calibrating a baseline transfer function for estimating a percentage loss of $E_{\mathit{eff}}$ as a function of resonant frequency, the laboratory tests may be used to determine a threshold percentage loss of $E_{\mathit{eff}}$(axial) that may be used to make decisions in the field. Specifically, this threshold percentage loss may be a maximum acceptable percentage loss of the effective elastic modulus of the cable for use in the wellbore. The threshold percentage loss may be determined based on the maximum stress, breaking strain, and other points of the stress-strain curves calculated for the different samples. For example, the maximum stress in the stress-strain curve for a sample with a 10 percent loss of $E_{\mathit{eff}}$(axial) may be well above the maximum stress expected to be encountered on the composite slickline cable 30 throughout its use. However, the maximum stress in the curve for a sample with a 20 percent loss of $E_{\mathit{eff}}$ may be only just above or slightly below the expected maximum stress. Accordingly, it may be desirable to use 10 percent as the threshold percentage loss, in order to prevent yielding or failure of the composite cable during its field use.

The threshold percentage loss of $E_{\mathit{eff}}$(axial) may be determined based on business needs, such as the expected amount of weight to be lowered/lifted via the cable as well as other factors. Once a composite cable in the field reaches the threshold percentage loss of effective elastic modulus, the cable may be put away and not used again after that trip. Thus, the elastic modulus measurement system 50 may be used to assess and guarantee the mechanical reliability of the composite slickline cable 30 by alerting an operator when the cable reaches an undesirable loss of effective elastic modulus over the threshold.

Figure 7:
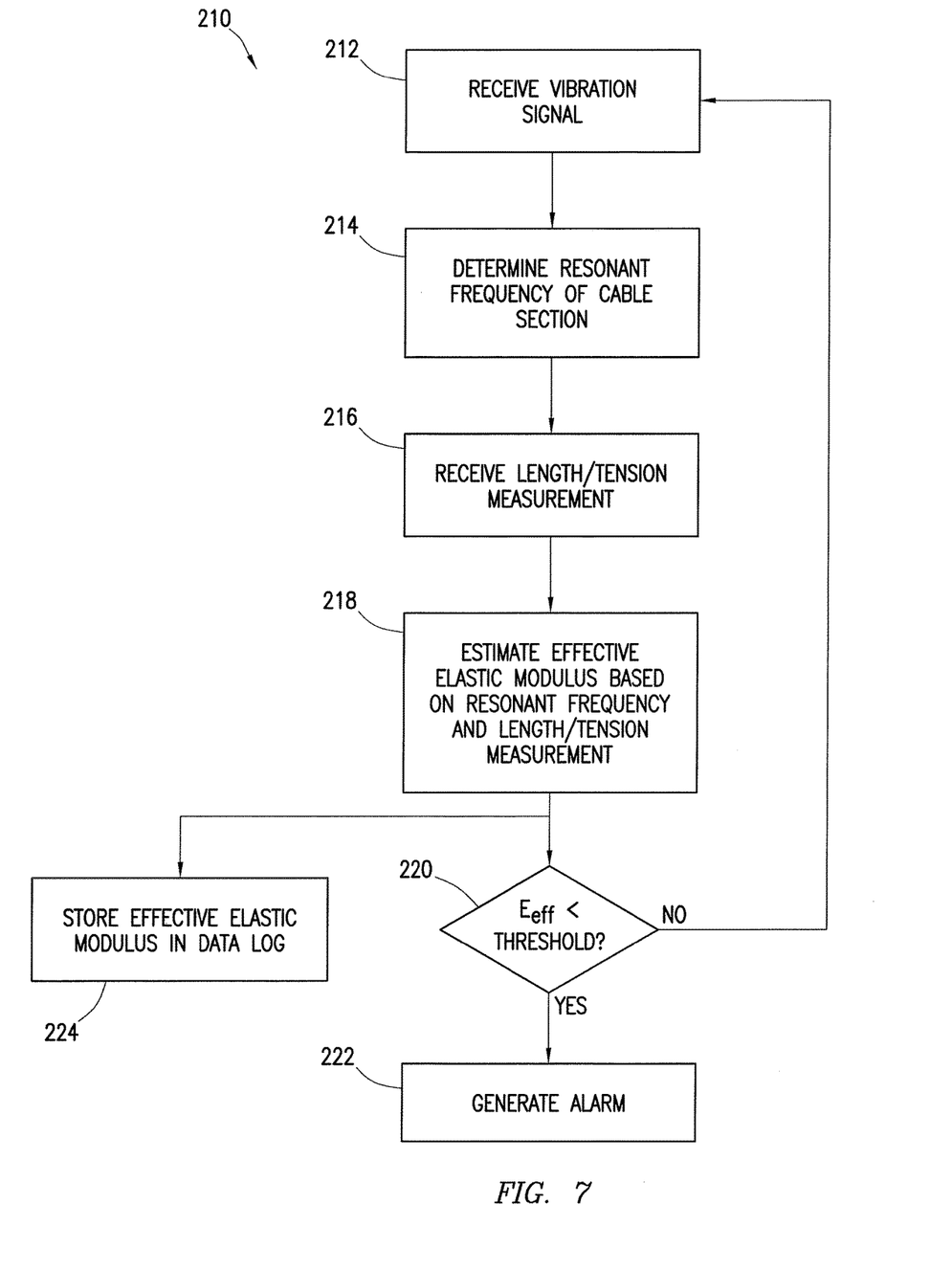
FIG. 7 is a process flow diagram illustrating a method for performing in-situ inspections of the mechanical fatigue on a composite slickline, in accordance with an embodiment of the present disclosure.

The calibrated model and threshold percentage loss may then be used in the signal processing unit 60 for composite cable non-destructive inspection purposes. FIG. 7 illustrates a method 210 for operating the signal processing unit 60 to provide this mechanical inspection. The method 210 may include receiving (block 212) a vibration signal indicative of vibration of the composite cable section, via the vibration analyzer. The method 210 also may include determining (block 214) a resonant frequency of the composite cable section based on the vibration signal via the signal processing unit of the vibration analyzer. In addition, the method 210 may include receiving (block 216) a length and/or tension measurement at the signal processing unit. The length and/or tension measurements may be taken via a tension sensor, optical sensor, or other device positioned near the spool from which the composite cable is unwound. The length and/or tension measurement may be indicative of the length of the composite cable extending downhole and the overall tension on the composite cable from the weight of the subsurface device and the cable itself.

The method 210 may include estimating (block 218) an effective elastic modulus of the composite cable based on the detected resonant frequency and based on the measured length and/or tension. This may involve applying a correction to the determined resonant frequency to adjust the frequency in a way that accounts for the length and/or weight of the downhole cable portion. As described above, the frequency change is generally proportional to the length of the cable, so a simple adjustment can be determined. With the corrected resonant frequency, the signal processing unit may estimate the effective elastic modulus (or a change in the effective elastic modulus) using a calibration model developed from laboratory tests, as described above. In other embodiments, the estimation may involve determining an estimated effective elastic modulus corresponding to the detected resonant frequency and then adjusting the elastic modulus estimate to account for the length/weight of the downhole cable.

In further embodiments, the method 210 may include comparing (block 220) the estimated effective elastic modulus (or percentage loss in effective elastic modulus) with a threshold value. If the effective elastic modulus (or percentage loss) is less than the threshold value, the method 210 may be repeated and the well servicing operation can be continued. If the effective elastic modulus (or percentage loss) is greater than or equal to the threshold, though, the method 210 may include generating (block 222) an alarm or alert to notify the operators that the composite cable has reached its usage limit. After the composite cable reaches this point, the operators may remove and replace the composite cable with one that has a higher effective elastic modulus to perform well servicing operations.

Further, in some embodiments the method 210 may include storing (block 224) the effective elastic modulus in a data log. The elastic modulus measuring system may be designed to take readings of the elastic modulus (e.g., using the method 210) periodically over time. The determined effective elastic modulus of the cable may be stored in the log after each reading for wire fatigue management. That is, an operator may be able to track the changes in elastic modulus of the composite slickline over time using information stored in the log, in order to make decisions based on the observed effects of mechanical fatigue in the cable. In addition, tension readings, downhole depth readings, and/or other sensor readings may be stored in the data log periodically over time as well. These readings may be correlated with the elastic modulus readings in order to determine the effect of changes in certain elements of the drilling environment to the strength of the slickline cable. All the collected data in the log may be analyzed to provide a characterization of the slickline cable at a certain point in time.

Embodiments disclosed herein include:

A. A composite cable inspection system including a sensing assembly for sensing vibration of a section of a cable disposed through the sensing assembly at a position above a wellhead. The composite cable inspection system also includes a vibration generator disposed adjacent to the sensing assembly for generating vibrations in the section of the cable without directly impacting the section of the cable. Further, the composite cable inspection system includes a signal processing unit in communication with the sensing assembly for determining an effective elastic modulus of the cable based on a detected vibration mode frequency of the section of the cable.

B. A method including maintaining a tension on a section of a cable disposed between pulleys in a sensing head assembly by applying weight to the cable from a subsurface device disposed at a distal end of the cable. The method also includes exciting the section of the cable between the pulleys to cause the section of the cable to vibrate via a vibration generator disposed in the sensing head assembly. In addition, the method includes detecting a vibration of the section of the cable via a sensor disposed in the sensing head assembly. Further, the method includes determining an effective elastic modulus of the cable based on the detected vibration via a signal processing unit communicatively coupled to the sensor.

C. A method including receiving a signal at a signal processing unit indicative of a vibration of a section of a fiber reinforced composite cable disposed at least partially in a wellbore. The method also includes determining a resonant frequency of the section of the cable based on the vibration signal. The method further includes estimating an effective elastic modulus of the cable based at least on the resonant frequency of the section of the cable.

Each of the embodiments A, B, and C may have one or more of the following additional elements in combination: Element 1: wherein the sensing assembly includes a pair of pulleys to form boundaries of the section of the cable disposed between the pulleys. Element 2: wherein the vibration generator includes a piezoelectric motor coupled to one of the pair of pulleys to vibrate the section of the cable. Element 3: wherein the vibration generator includes a gas gun nozzle or a water gun nozzle. Element 4: further including a data acquisition unit in communication with the vibration generator and with the signal processing unit. Element 5: wherein the sensing assembly includes an optical vibration analyzer having a laser source and a photo-detector for detecting the vibration of the section of the cable. Element 6: wherein the optical vibration analyzer further includes a pin-hole formed proximate the photo-detector to limit an amount of light directed to the photo-detector. Element 7: wherein the signal processing unit includes a look-up table or calibration model for determining the effective elastic modulus of the cable based on a laboratory test calibration relating resonant frequency to elastic modulus. Element 8: wherein the sensor assembly includes a component of the vibration generator, a pair of pulleys, a vibration analyzer, and the signal processing unit disposed in a housing. Element 9: wherein the signal processing unit is communicatively coupled to a sensor in the sensing assembly to detect a resonant frequency of the vibrating section of the cable and to determine the effective elastic modulus based on the detected resonant frequency.

Element 10: further including determining a resonant frequency of the detected vibration and determining the effective elastic modulus based on the resonant frequency via the signal processing unit. Element 11: further including comparing a detected shift in the resonant frequency with laboratory results to determine a corresponding decrease in the effective elastic modulus. Element 12: further including detecting the vibration of the section of the cable by outputting light toward the section of the cable via a laser source and measuring an amount of light reflected from the section of the cable via a photo-detector. Element 13: further including comparing the effective elastic modulus to an elastic modulus threshold value to determine whether the cable has reached the end of its operational life. Element 14: further including determining the elastic modulus of the cable while maintaining contact with the section of the cable only at contact points where the cable touches the pulleys.

Element 15: further including receiving a signal at the signal processing unit indicative of a length of the cable in the wellbore or a tension on the cable, and estimating the effective elastic modulus based on the resonant frequency and based on the length of, or the tension on, the cable. Element 16: further including adjusting the determined resonant frequency based on the length of, or the tension on, the cable to determine an adjusted resonant frequency value, and estimating the effective elastic modulus based on the adjusted resonant frequency value. Element 17: further including comparing the estimated effective elastic modulus to a threshold, and if the effective elastic modulus is less than the threshold, generating an alarm to alert an operator to a status of the cable. Element 18: further including storing the estimated effective elastic modulus in a log for tracking the mechanical fatigue of the cable.

Although the present disclosure and its advantages have been described in detail, it should be understood that various changes, substitutions and alterations can be made herein without departing from the spirit and scope of the disclosure as defined by the following claims.

What is claimed is:

1. A composite cable inspection system comprising:
a sensing assembly for sensing vibration of a section of a cable disposed through the sensing assembly at a position above a wellhead;
a vibration generator disposed adjacent to the sensing assembly for generating vibrations in the section of the cable without directly impacting the section of the cable; and
a signal processing unit in communication with the sensing assembly for determining an effective elastic modulus of the cable based on a detected vibration mode frequency of the section of the cable.

2. The system of claim 1, wherein the sensing assembly comprises a pair of pulleys to form boundaries of the section of the cable disposed between the pulleys.

3. The system of claim 2, wherein the vibration generator comprises a piezoelectric motor coupled to one of the pair of pulleys to vibrate the section of the cable.

4. The system of claim 1, wherein the vibration generator comprises a gas gun nozzle or a water gun nozzle.

5. The system of claim 1, further comprising a data acquisition unit in communication with the vibration generator and with the signal processing unit.

6. The system of claim 1, wherein the sensing assembly comprises an optical vibration analyzer having a laser source and a photo-detector for detecting the vibration of the section of the cable.

7. The system of claim 6, wherein the optical vibration analyzer further comprises a pin-hole formed proximate the photo-detector to limit an amount of light directed to the photo-detector.

8. The system of claim 1, wherein the signal processing unit comprises a look-up table or calibration model for determining the effective elastic modulus of the cable based on a laboratory test calibration relating resonant frequency to elastic modulus.

9. The system of claim 1, wherein the sensor assembly comprises a component of the vibration generator, a pair of pulleys, a vibration analyzer, and the signal processing unit disposed in a housing.

10. The system of claim 1, wherein the signal processing unit is communicatively coupled to a sensor in the sensing assembly to detect a resonant frequency of the vibrating section of the cable and to determine the effective elastic modulus based on the detected resonant frequency.

11. A method, comprising:
maintaining a tension on a section of a cable disposed between pulleys in a sensing head assembly by applying weight to the cable from a subsurface device disposed at a distal end of the cable;
exciting the section of the cable between the pulleys to cause the section of the cable to vibrate via a vibration generator disposed in the sensing head assembly;
detecting a vibration of the section of the cable via a sensor disposed in the sensing head assembly; and
determining an effective elastic modulus of the cable based on the detected vibration via a signal processing unit communicatively coupled to the sensor.

12. The method of claim 11, further comprising determining a resonant frequency of the detected vibration and determining the effective elastic modulus based on the resonant frequency via the signal processing unit.

13. The method of claim 12, further comprising comparing a detected shift in the resonant frequency with laboratory results to determine a corresponding decrease in the effective elastic modulus.

14. The method of claim 11, further comprising detecting the vibration of the section of the cable by outputting light toward the section of the cable via a laser source and measuring an amount of light reflected from the section of the cable via a photo-detector.

15. The method of claim 11, further comprising comparing the effective elastic modulus to an elastic modulus threshold value to determine whether the cable has reached the end of its operational life.

16. A method, comprising:
receiving a signal at a signal processing unit indicative of a vibration of a section of a fiber reinforced composite cable disposed at least partially in a wellbore;
determining a resonant frequency of the section of the cable based on the vibration signal; and
estimating an effective elastic modulus of the cable based at least on the resonant frequency of the section of the cable.

17. The method of claim 16, further comprising:
receiving a signal at the signal processing unit indicative of a length of the cable in the wellbore or a tension on the cable; and
estimating the effective elastic modulus based on the resonant frequency and based on the length of, or the tension on, the cable.

18. The method of claim 17, further comprising:
adjusting the determined resonant frequency based on the length of, or the tension on, the cable to determine an adjusted resonant frequency value; and
estimating the effective elastic modulus based on the adjusted resonant frequency value.

19. The method of claim 16, further comprising:
comparing the estimated effective elastic modulus to a threshold; and
if the effective elastic modulus is less than the threshold, generating an alarm to alert an operator to a status of the cable.

20. The method of claim 16, further comprising storing the estimated effective elastic modulus in a log for tracking the mechanical fatigue of the cable.

* * * * *